(12) United States Patent
Robles et al.

(10) Patent No.: US 11,744,747 B2
(45) Date of Patent: *Sep. 5, 2023

(54) ABSORBENT ARTICLE WITH DUAL CORE

(71) Applicant: The Procter & Gamble Company, Cincinnati, OH (US)

(72) Inventors: Miguel Alvaro Robles, Wyoming, OH (US); Bruce William Lavash, West Chester, OH (US); Sion Agami, Mason, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 648 days.

This patent is subject to a terminal disclaimer.

(21) Appl. No.: 16/750,460

(22) Filed: Jan. 23, 2020

(65) Prior Publication Data
US 2020/0155378 A1  May 21, 2020

Related U.S. Application Data

(63) Continuation of application No. 15/493,662, filed on Apr. 21, 2017, now Pat. No. 10,583,053, which is a
(Continued)

(51) Int. Cl.
*A61F 13/15* (2006.01)
*A61F 13/536* (2006.01)
(Continued)

(52) U.S. Cl.
CPC ...... *A61F 13/536* (2013.01); *A61F 13/15203* (2013.01); *A61F 13/472* (2013.01); *A61F 13/47245* (2013.01); *A61F 13/534* (2013.01); *A61F 13/535* (2013.01); *A61F 13/537* (2013.01); *A61F 13/538* (2013.01);
(Continued)

(58) Field of Classification Search
CPC .. A61F 13/532; A61F 13/5323; A61F 13/533; A61F 2013/530583; A61F 2013/530481; A61L 15/425; A61L 15/24
See application file for complete search history.

(56) References Cited

U.S. PATENT DOCUMENTS 2,335,810 A    11/1943  Stalkup
5,147,345 A *   9/1992  Young ............... A61F 13/49466
                                                      604/374

(Continued)

FOREIGN PATENT DOCUMENTS

JP    2005152250    6/2005
JP    2007061473    3/2007
(Continued)

OTHER PUBLICATIONS

All Office Actions, U.S. Appl. No. 13/672,499.
(Continued)

*Primary Examiner* — Jacqueline F Stephens
(74) *Attorney, Agent, or Firm* — William E. Gallagher

(57) ABSTRACT

An absorbent article. The absorbent article includes a topsheet having a body contacting surface, a backsheet joined to said topsheet, and an absorbent core disposed between the topsheet and the backsheet, wherein the absorbent core has an upper layer and a lower layer.

8 Claims, 8 Drawing Sheets

Related U.S. Application Data continuation of application No. 13/672,499, filed on Nov. 8, 2012, now Pat. No. 9,649,228.

(60) Provisional application No. 61/557,723, filed on Nov. 9, 2011.

(51) Int. Cl.

| | | |
|---|---|---|
| *A61F 13/538* | (2006.01) | |
| *A61F 13/537* | (2006.01) | |
| *A61F 13/472* | (2006.01) | |
| *A61F 13/534* | (2006.01) | |
| *A61F 13/535* | (2006.01) | |
| *A61L 15/26* | (2006.01) | |
| *A61L 15/42* | (2006.01) | |
| *A61F 13/53* | (2006.01) | |

(52) U.S. Cl.
CPC ............ *A61L 15/26* (2013.01); *A61L 15/425* (2013.01); *A61F 2013/5355* (2013.01); *A61F 2013/530817* (2013.01); *A61F 2013/530861* (2013.01)

(56) References Cited

U.S. PATENT DOCUMENTS

| | | |
|---|---|---|
| 5,219,341 A | 6/1993 | Serbiak |
| 5,242,435 A | 9/1993 | Murji |
| 5,306,267 A | 4/1994 | Hahn |
| 5,348,547 A | 9/1994 | Payne et al. |
| 5,387,207 A * | 2/1995 | Dyer ................. A61F 13/53747 521/64 |
| 5,624,423 A | 4/1997 | Anjur et al. |
| 5,649,916 A | 7/1997 | Dipalma |
| 5,807,362 A | 9/1998 | Serbiak |
| 5,899,893 A | 5/1999 | Dyer |
| 6,171,291 B1 | 1/2001 | Osborn, III et al. |
| 6,245,410 B1 | 6/2001 | Haehnle |
| 6,534,149 B1 | 3/2003 | Daley et al. |
| 6,570,057 B1 | 5/2003 | Schmidt |
| 6,582,411 B1 | 6/2003 | Carstens |
| 6,649,809 B2 | 11/2003 | Fields |
| 6,821,270 B2 | 11/2004 | Rosenfeld |
| 6,852,905 B2 | 2/2005 | Baker |
| 6,899,701 B2 | 5/2005 | Carstens et al. |
| 7,037,298 B2 | 5/2006 | Ohshima et al. |
| 7,235,708 B2 | 6/2007 | Guidotti |
| 7,597,689 B2 | 10/2009 | Hoffmann |
| 8,754,286 B2 | 6/2014 | Bergstrom et al. |
| 9,649,228 B2 | 5/2017 | Robles |
| 10,583,053 B2 * | 3/2020 | Robles .................. A61L 15/425 |
| 2003/0153890 A1 | 8/2003 | Rosenfeld |
| 2003/0181884 A1 | 9/2003 | Carstens et al. |
| 2004/0078016 A1 | 4/2004 | Baker |
| 2004/0193129 A1 | 9/2004 | Guidotti et al. |
| 2006/0184150 A1 * | 8/2006 | Noel ................. A61F 13/15203 604/383 |
| 2007/0225669 A1 * | 9/2007 | Dyer .................. A61F 13/2065 604/368 |
| 2013/0116646 A1 | 5/2013 | Robles |

FOREIGN PATENT DOCUMENTS

| | | |
|---|---|---|
| JP | 2009100846 | 5/2009 |
| JP | 2009207598 | 9/2009 |
| JP | 2009261777 | 11/2009 |
| JP | 4508861 | 5/2010 |
| JP | 4912069 | 1/2012 |
| WO | WO0185083 A1 | 11/2001 |
| WO | WO2012102057 A1 | 8/2012 |

OTHER PUBLICATIONS

All Office Actions, U.S. Appl. No. 15/493,662.
International Search Report and Written Opinion; Application Ser. No. PCT/US2012/064141; dated Jan. 30, 2013, 8 pages.
Third Party Opposition filed for European Patent Application Ser. No. 12795169.7,dated Nov. 6, 2013, 13 pages.

\* cited by examiner

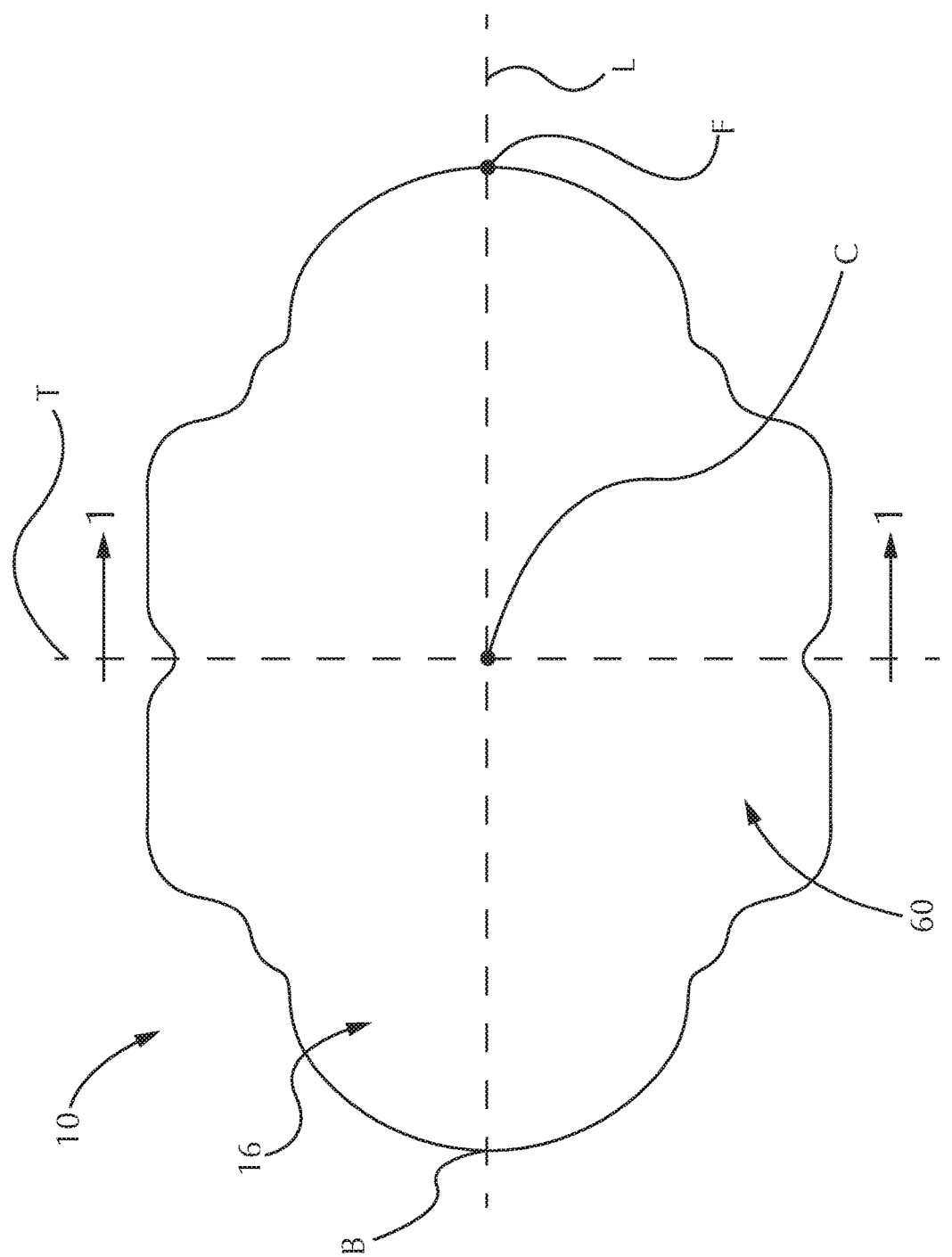

ABSORBENT ARTICLE WITH DUAL CORE

CROSS REFERENCE TO RELATED APPLICATION

This application is a continuation of, and claims priority under 35 U.S.C. § 120 to, U.S. patent application Ser. No. 15/493,662, filed on Apr. 21, 2017, which is a continuation of U.S. patent application Ser. No. 13/672,499, filed Nov. 8, 2012, now U.S. Pat. No. 9,649,228, issued on May 16, 2017, which claims the benefit, under 35 USC § 119(e), of U.S. Provisional Patent Application Ser. No. 61/557,723, filed on Nov. 9, 2011, the entire disclosures of which are fully incorporated by reference herein.

FIELD OF INVENTION

This application relates to absorbent articles, such as sanitary napkins, for the absorption of menses. More particularly, the present invention relates to absorbent articles utilizing multiple absorbent cores which have an improved comfort and fit.

BACKGROUND OF THE INVENTION

Unlike many types of disposable absorbent articles, absorbent articles such as pads and pantiliners are specifically designed to acquire menstrual fluid. Menstrual fluid differs from other exudates, such as urine, in many important properties, such as viscosity. Therefore, absorbent articles should differ in their structural components from devices such as baby diapers to be optimized for the maximum absorption of menstrual fluid.

For absorbent articles, the fluid insult has very different characteristics, in the context of physio-chemical properties (e.g., viscosity, fluid dynamics, etc.), volume, and time to be absorbed. For example, menstrual flow typically consists of two patterns. One of these is "trickle" flow, which varies from 0.1 to 2 ml per hour. The second pattern is "gush" flow which varies from a few ml in volume delivered over a few seconds. Gush flow can result from an accumulation of menses pooling in the vagina which can then exit the body upon a change in position, such as a transition from sitting to standing. In any event, even with gush flow, the total amount of fluid required to be absorbed into the core in a given time is much less than that required by other absorbent products, such as baby diapers, for example. One practical result is that menstrual absorbent articles, rather than needing to be designed to handle gushing fluid, more typically handle fluid through a "blotting" effect. However, a need exists to be able to handle occasional gush at the point of exit through improved absorption where it is needed the most.

One possible method to improve absorbency is to increase the width or thickness of the absorbent article. However, this approach can represent a less comfortable pad for the consumer. This is due to the relationship between the body and the pudendal region. The body is naturally narrow in the front region and becomes broader towards the back. However, the pudendal region is found in the front and most of the discharge exits the body in the front region. This creates a tradeoff between comfort and increased protection.

Additionally, there is a continuing need for an absorbent article that has improved body fit to better fit the body of the wearer while not sacrificing absorbency.

Additionally, there is a continuing need for providing guidance and assistance to consumers on how to place an absorbent article for better body fit and improved absorbency.

SUMMARY OF THE INVENTION

An absorbent article is disclosed. The absorbent article includes a topsheet having a body contacting surface and a lower surface opposite the body contacting surface, a backsheet joined to the topsheet, and an absorbent core disposed between the topsheet and the backsheet. The absorbent core has an upper layer comprising an upper surface and a lower surface opposite the upper surface and a lower layer comprising an upper surface and a lower surface opposite the upper surface. The upper layer includes an open celled foam and the lower layer includes a fibrous network. The absorbent article has a transverse center line. The absorbent core upper layer perimeter comprises a longitudinal axis and a transverse axis center axis dividing the absorbent core upper layer perimeter into a section one and a section two. The upper layer section one has a surface area that is at least 5% greater than the surface area of section two.

An absorbent article is further disclosed. The absorbent article includes a topsheet having a body contacting surface and a lower surface opposite the body contacting surface, a backsheet joined to the topsheet, and an absorbent core disposed between the topsheet and the backsheet, wherein the absorbent core comprises an upper layer comprising an upper surface and a lower surface opposite the upper surface and a lower layer comprising an upper surface and a lower surface opposite the upper surface. The absorbent article has a transverse center line. The absorbent core upper layer perimeter comprises a longitudinal axis and a transverse axis center axis dividing the absorbent core upper layer perimeter into a section one and a section two. The upper layer section one has a surface area that is at least 5% greater than the surface area of section two. The absorbent core lower layer perimeter comprises a longitudinal axis and a transverse axis center axis dividing the absorbent core lower layer perimeter into a section one and a section two. The lower layer section one has a surface area that is at least 5% greater than the surface area of section two.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

FIG. 1A is a plan view of the backsheet of an absorbent article.

DETAILED DESCRIPTION OF THE INVENTION

Figure 1:
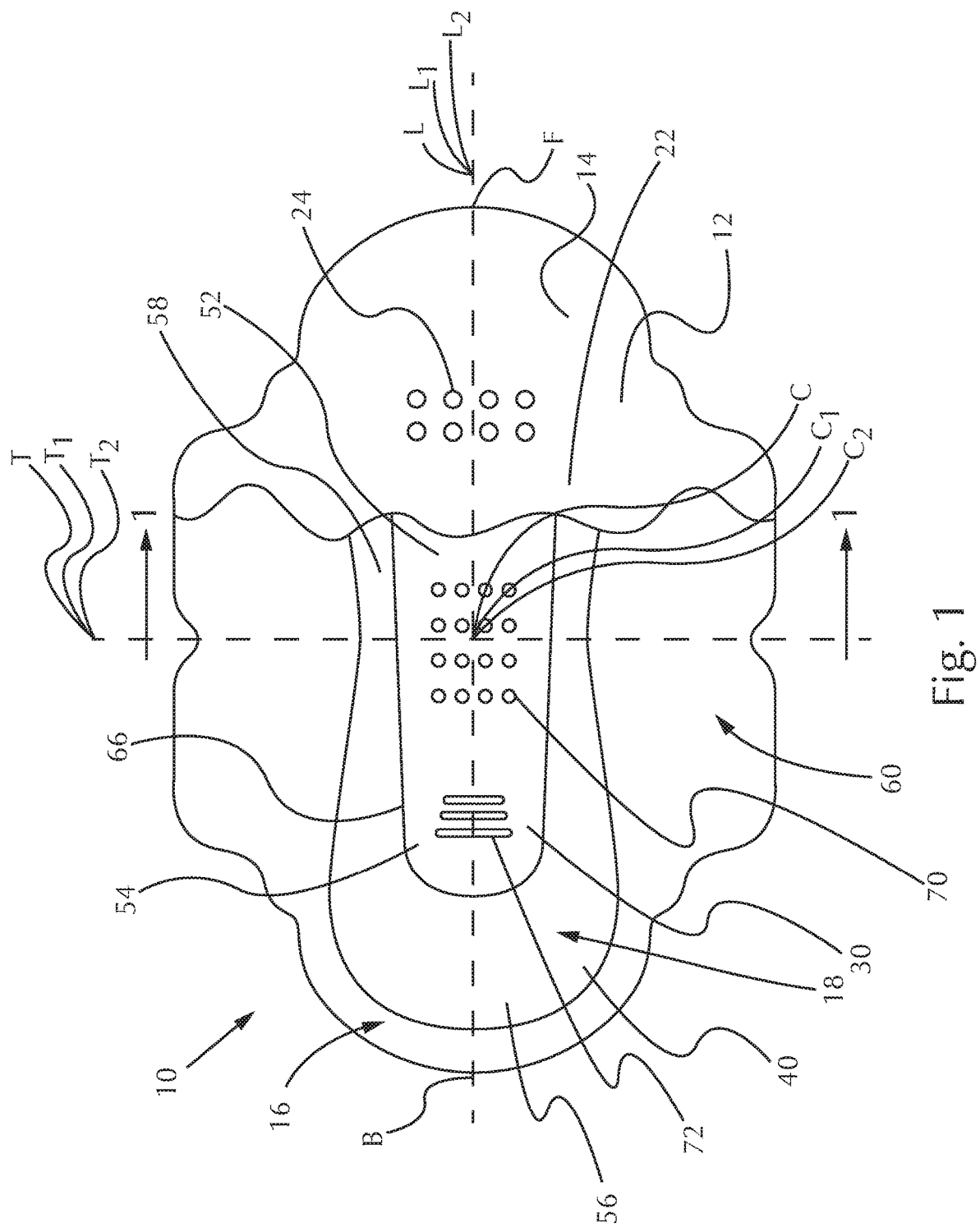
FIG. 1 is a plan view of an absorbent article having an absorbent core having two separate layers where the top layer is asymmetric.

As used herein, absorbent articles include pantiliners, catamenial pads, sanitary napkins, menstrual pads, and the like.

As used herein, the term "absorbent core" refers to the component of the absorbent article that is primarily responsible for the liquid handling properties of the article, including acquiring, distributing, and storing body liquids. As such, the absorbent core typically does not include the topsheet or backsheet of the absorbent article.

As used herein, the term "asymmetric" means having no symmetry about at least one axis.

The terms "body-contacting surface" and "wearer-contacting surface" are used interchangeably herein and refer to one or more surfaces of any article component that is intended to be worn or positioned toward or adjacent the body of the wearer/user for contact between the wearer/user and the article's surface at some time during the use period. The term "garment surface" as used herein refers to the outer or exterior surface of any article component that is intended to be worn or positioned adjacent a wearer's undergarments, or in the case of an absorbent article which is not worn by the user, the garment surface is typically positioned adjacent a user's hand or other implement assisting in the use of the absorbent article. As used herein, the term "wearer" and "user" are used interchangeably as the present invention contemplates absorbent articles which may not be intended to be worn, but rather used to absorb bodily exudates.

As used herein, the terms "body liquids," "body fluids," or "body exudates" include, but are not limited to menses, vaginal discharges, blood, sweat, and combinations of these substances.

As used herein, the term "flexible" refers to materials which are compliant and readily conform to the general shape and contours of the wearer's body under normal body-imposed forces.

As used herein, the term "foam" is synonymous with the term "cellular polymer," which includes materials having a significant void volume, typically greater than 75%. "Open-celled" foams further have a reticulated internal structure disposed therein comprising relatively thin "strut" elements interconnected and forming cells or pores providing for fluid communication throughout the structure. Mean cell diameters refer to the diameter of the pores in the foam visible by microscopy. The pores tend to be relatively spherical in shape and the mean diameter can be measured by using microscopic techniques. One suitable technique is to use a scanning electron micrograph and measure the apparent mean diameter of at least 25 representative cells to determine the mean. The density of foams can be determined using uncompressed samples of said foams devoid of contaminants such as water, and measuring the volume and weight of the foam. A cubic sample having an edge length greater than or equal to 2 cm is practical.

As used herein, "hydrophilic" refers to a material or substance having affinity for water or aqueous fluids. In general, a hydrophilic surface will have a contact angle with water of less than 60°, or even less than 30°.

As used herein, the term "inorganic" refers to a material which is not organic in nature. As used herein, the term "organic" refers to compounds of carbon.

As used herein the term "joined" refers to the condition where a first member is attached, or connected, to a second member either directly or indirectly. Where the first member is attached, or connected, to an intermediate member which in turn is attached, or connected, to the second member, the first member and second member are joined indirectly.

As used herein, the term "layer" refers to a three dimensional structure having two dimensions that are substantially greater than the third dimension. The term layer is not limited to single layers or sheets of material. Thus a layer may comprise laminates or combinations of several sheets or webs of the requisite type of materials. Accordingly, the term "layer" includes the terms "layers" and "layered."

As used herein, the term "lower layer" refers to the layer that serves to acquire gushes, control wicking of exudates, and/or store the fluid. A portion of the lower layer remains in close capillary contact with the upper layer. The lower layer can be referred to as a fluid storage layer.

As used herein, the term "microfibers" refers to fibers having an average effective diameter of 0.1 micron to 6 microns and an aspect ratio of at least 100. The aspect ratio of a microfiber is the contour length of the fiber divided by the average effective diameter of the fiber. The contour length of a fiber is the length of the fiber in a substantially straightened condition. Long microfibers can have aspect ratios which exceed $1 \times 10^{12}$. The microfiber may be of any configuration, including but not limited to straight, curled, kinked, crimped, and combinations thereof. The cross sectional area of the microfiber orthogonal to its contour length at any point may have any geometric shape, including but not limited to circular (round), square, flat, oval, star-shaped, irregular, and combinations thereof. For fibers having a non-circular cross section, the effective diameter is the diameter of a circle having a cross sectional area equal to that of the fiber. Microfibers may comprise any material, including but not limited to natural polymers, synthetic polymers, minerals, glass, ceramics, metals, vegetable matter, animal matter, carbon, and combinations thereof. A sample of microfibers having an average effective diameter between 0.1 and 6 microns may contain individual fibers with diameters greater than 6 microns and/or individual fibers with diameters less than 0.1 micron.

"Non-biopersistent" refers to microfibers comprising at least 18% alkaline and alkaline earth oxides and meet at least one of the criteria for lack of biopersistence listed below. A non-biopersistent material according to the present invention can also meet the criteria of the German Dangerous Substances Ordinance (Gefahrstoffverordnung) Annex V, No. 7.1(1). A suitable method for selecting a fiber composition to test for non-biopersistence of certain fibers according to the test method below is to use the method reported by Eastes, W., Potter, R. M., and Hadley, J. G. (2000), "Estimation of Dissolution Rate from In-Vivo Studies of Synthetic Vitreous Fibers,"*Inhalation Toxicology,* 12(11), 1037-1054. An online calculator implementing the method can be found at http://fiberscience.owenscorning.com/kdis-app.html. This calculator predicts the rate of biodissolution as a function of the chemical composition of the fiber. A non-biopersistent fiber meets at least one of the following criteria: (1) a short-term biopersistence test by inhalation showing that the fibers longer than 20 um have a weighted half-life of less than 10 days (a suitable short-term biopersistence test by inhalation is described in European Union protocol ECB/TM/26 rev. 7), or (2) a short-term biopersistence test by intratracheal instillation showing that the fibers longer than 20 um have a weighted half-life less than 40 days (a suitable short-term biopersistence test by intratracheal instillation is described in European Union protocol ECB/TM/27 rev. 7), or (3) an appropriate intraperitoneal test showing no evidence of excess carcinogenicity (a suitable test for carcinogenicity of inorganic vitreous microfibers after intra peritoneal injection in rats is described in European Union protocol ECB/TM/18(97)), or (4) a suitable long-term inhalation test showing the absence of relevant pathogenicity or neoplastic changes (A suitable long-term inhalation test is described in European Union protocol ECB/TM/17(97)). These test methods are reported in European Commission Joint Research Centre Institute for Health and Consumer Protection Unit: Toxicology and Chemical Substances, European Chemicals Bureau (1999), "Methods for the Determination of the Hazardous Properties for Human Health of Man Made Mineral Fibres (MMMF)," Report 18748, David M. Bernstein and Juan M. Riego Sintes Eds.

As used herein, the term "perimeter" refers to the outer limits of an area defined by a grouping of one or more smaller items.

As used herein, the term "pudendal" refers to the externally visible female genitalia.

As used herein, the term "superabsorbent" refers to a material capable of absorbing at least ten times its dry weight of a 0.9% saline solution at 25° C. Superabsorbent polymers absorb fluid via an osmotic mechanism to form a gel. Superabsorbents may be particulates, fibers, foams, sheets, or other shapes.

As used herein, the term "symmetry" refers to an exact correspondence of form and constituent configuration on opposite sides of a dividing line or plane or about a center or an axis.

As used herein, the term "upper layer" refers to the layer which is in closer proximity to the body of the wearer of the article in use than the lower layer, such that the upper layer receives body fluids (menstrual fluid, blood, and the like) before the lower layer. The upper layer can be referred to as a fluid acquisition layer.

As used herein, the term "vitreous" refers to a material which is substantially non-crystalline in that the material comprises more than 90% amorphous material. A vitreous material can comprise more than 99% amorphous material.

Figure 1B:
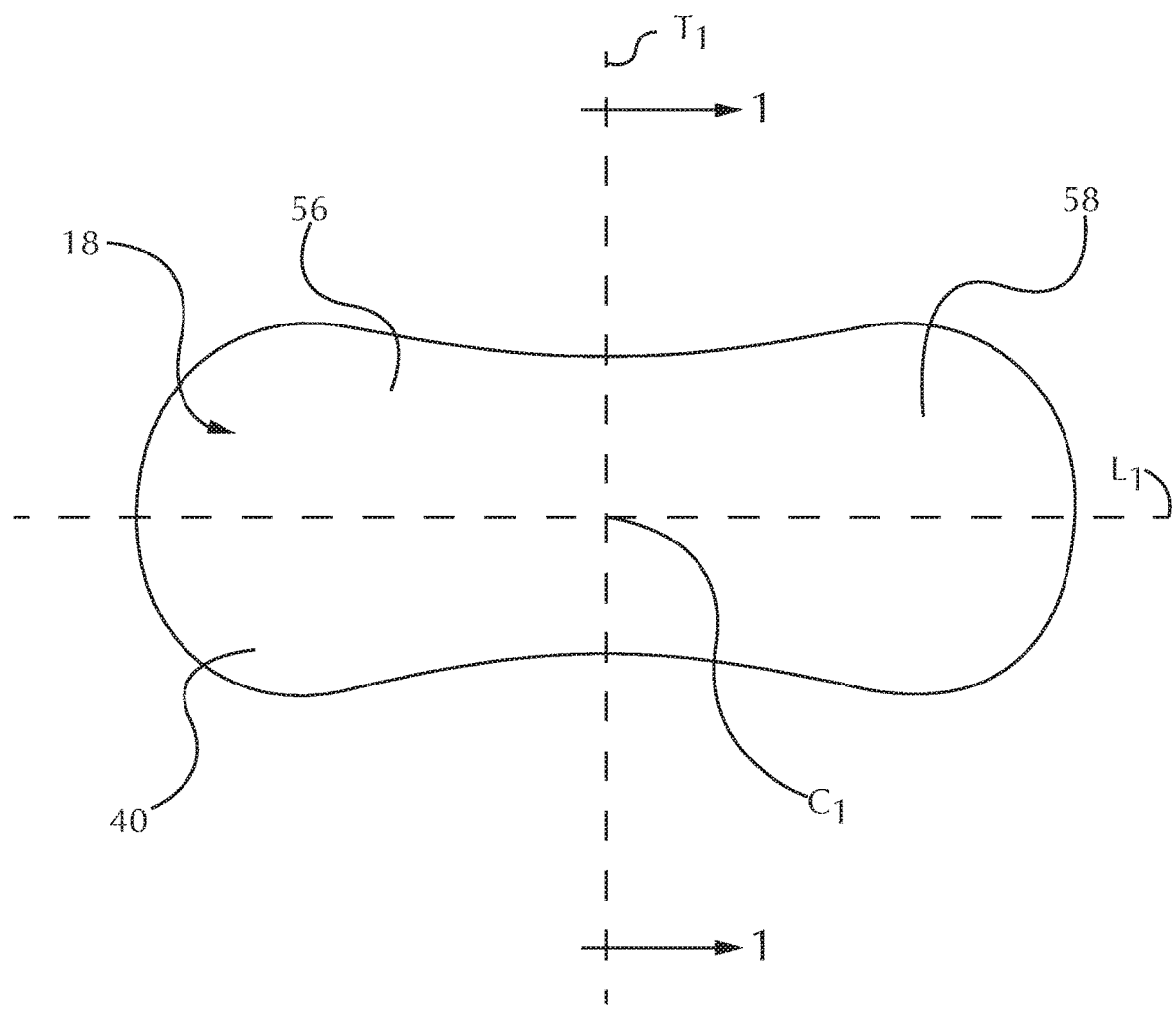
FIG. 1B is a plan view of the absorbent core lower layer of an absorbent article having an absorbent core having two separate layers where the top layer is asymmetrical.
Figure 1C:
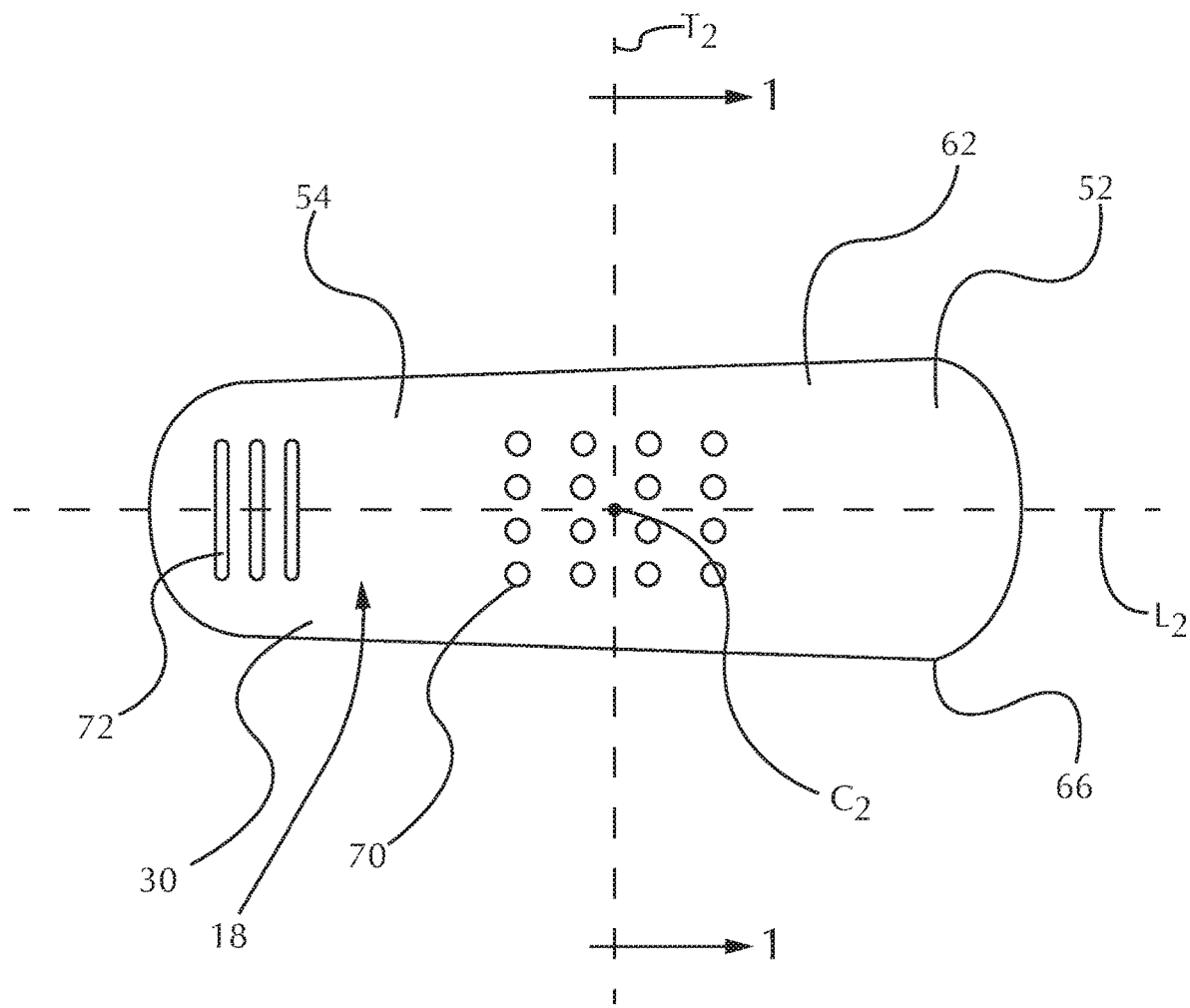
FIG. 1C is a plan view of the absorbent core upper layer of an absorbent article having an absorbent core having two separate layers where the top layer is asymmetrical.
Figure 1D:
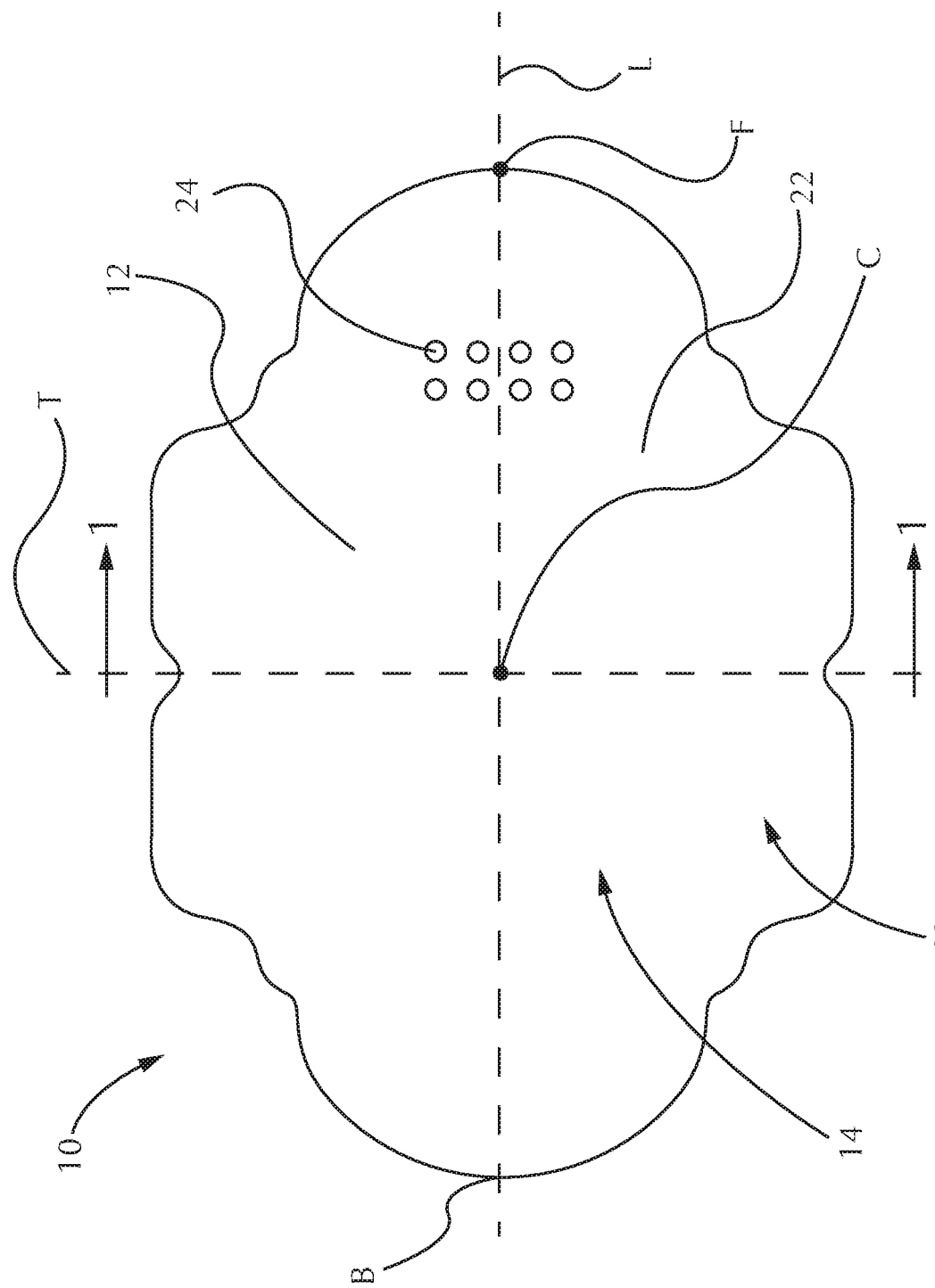
FIG. 1D is a plan view of the topsheet of an absorbent article.

FIG. 1 shows a plan view of an absorbent article 10. The absorbent article can have four basic layers including a liquid impervious backsheet 16, an absorbent core lower layer 40, an absorbent core upper layer 30, and a topsheet 14 joined to the backsheet. An absorbent core 18 including the absorbent core lower layer 40 and absorbent core upper layer 30 is disposed between the topsheet 14 and the backsheet 16. FIGS. 1A-1D show each of the four basic layers individually: FIG. 1A shows the backsheet 16, FIG. 1B shows the absorbent core lower layer 40, FIG. 1C shows the absorbent core upper layer 30, and FIG. 1D shows the topsheet 14.

The absorbent article 10 has a longitudinal axis L and a transverse axis T that meet at a central point C. The absorbent article 10 has a front point F and a back point B. The transverse axis T is located by taking the midpoint between the absorbent article 10 front point F and the back point B. The absorbent article 10 may also be provided with additional features commonly found in sanitary napkins, including "wings" or "flaps" 60 as is known in the art, and/or a fluid acquisition layer between the topsheet 14 and the absorbent core 18 to promote fluid transport from the topsheet 14 to the absorbent core 18.

The topsheet 14 of a sanitary napkin can have various optional characteristics, as is known in the art. For example, the topsheet 14 can have channels embossed or other textured surfaces therein to direct fluid flow. The topsheet 14 may also have apertures 24. Secondary topsheets, often called acquisition and/or distribution layers, can be bonded to the topsheet. Various visual signals, indicia, or other markings can be added, for example by ink jet printing a the topsheet upper surface 32 or a topsheet lower surface 35, as well as on the secondary topsheet, the absorbent core, or the backsheet. The topsheet 14 of the absorbent article 10 may have a lotion composition 22 disposed onto at least the body-contacting surface 12 thereof.

The backsheet 16 can be any known or otherwise effective backsheet material, provided that the backsheet prevents external leakage of exudates absorbed and contained in the absorbent article. Flexible materials suitable for use as the backsheet include, but are not limited to, woven and nonwoven materials, laminated tissue, polymeric films such as thermoplastic films of polyethylene and/or polypropylene, composite materials such as a film-coated nonwoven material, or combinations thereof.

The absorbent core 18 includes more than one layer. Each layer has a front point and a back point. The absorbent core 18 may include an absorbent core upper layer 30 and an absorbent core lower layer 40. The absorbent core may have two layers, as shown by the absorbent core upper layer 30 and the absorbent core lower layer 40 in FIG. 1 or additional layers, such as 3 layers or more. The absorbent core 18 may have a total thickness of 0.8 mm to 18 mm at its thickest point and 0.8 mm to 15 mm at its thinnest point.

The upper layer 30 of the absorbent core 18 has a perimeter 66. Additionally, each layer of the absorbent core 18 may have a longitudinal and a transverse axis. The transverse axis T1 of the absorbent core lower layer 40 may be different than the transverse axis T2 of the perimeter of the absorbent core upper layer 30 and the absorbent article transverse axis T. The transverse axis T2 is located by taking the midpoint between the front portion and the back portion outermost perimeter points of the upper layer 30. Similarly, the longitudinal axis L1 of the absorbent core lower layer 40 may be different than the longitudinal axis L2 of the perimeter of the absorbent core upper layer 30 and the absorbent article longitudinal axis L. L1 and T1 meet at a central point C1. L2 and T2 meet at Central Point C2.

The absorbent core 18 can have additional features in the upper layer 30, the bottom layer 40, or both the upper and lower layer. The additional features are not deducted from the total area of the absorbent core upper or lower layer when present. Absorbent core 18 additional features may be encompassed in a portion of a layer and do not serve as a break in the perimeter of the layer. The absorbent core 18 additional features may include slits, slots, apertures, and lateral stiffeners, The absorbent core upper layer 30 or the absorbent core lower layer 40 can have a plurality of laterally-oriented slots 72 having an average gap width of at least 1 mm prior to use. Slots 72 are considered laterally oriented if they have a major vector component at the longitudinal center line L that is perpendicular to the longitudinal center line. Slots 72 can be substantially parallel, generally linear slots that are each parallel to center line L, and, therefore, have no vector component in the longitudinal direction. However, slots 72 can have other configurations, including generally curved orientations. Absorbent core 18 may also have any number of holes 70. Absorbent core 18 can have additional modifications and features to facilitate desired bending and folding. For example, absorbent core 18 can have additional slits, apertures, perforations, lines of weakness, lateral stiffeners, and the like. In particular, in one embodiment a line of weakness such as perforations or a score line along at least a portion of the longitudinal center line L can aid in proper formation of a raised hump or ridge along the center line.

As shown in FIG. 1, apertures 24 can serve the additional benefit of capturing fluid and fluid components that would otherwise tend to run off of the absorbent article 10 and possibly soil the garments of the wearer. For example, if fluid were to run off toward the longitudinal end of the absorbent article 10 shown in FIG. 1, the portion 16 of apertures 24 could intercept the fluid as it progressed, permitting a relatively unobstructed passage to an underlying absorbent core 18. These apertures 24 may also serve as indicia regarding the placement of the absorbent article 10 regarding the pudendal region and the undergarment.

FIG. 1B shows the absorbent core lower layer 40. The absorbent core lower layer 40 is approximately no greater than 25000 mm$^2$, 16000 mm$^2$ 9000 mm$^2$, 4000 mm$^2$, 1000 mm$^2$, or even less total surface area on any one surface, such as, for example approximately 2500 mm$^2$. Alternatively, the absorbent core lower layer covers no greater than 95%, 90%, 85%, 80%, 75%, 70%, 65%, 60%, 55%, 50%, 45%, 40%, 35%, 30%, 25%, 20%, 15%, 10% of the backsheet 16. As seen in FIG. 1b, the absorbent core lower layer 40 is divided by T1 into lower layer section one 56 and lower layer section two 58. Lower layer section one 56 has a surface area that is at least 5%, 10%, 15%, 20%, 25%, 30%, 35%, 40%, 45%, 50%, 55%, 60%, 61%, up to 100% greater than the surface area of lower layer section two 58. Alternatively, lower layer section one 56 may equal lower layer section two 58 in total surface area. T1 may overlay T and/or T2. The absorbent core lower layer 40 may consist of any geometric shape commonly known.

The absorbent core lower layer 40 can have a fibrous network including microfibers. One suitable microfiber is a non-biopersistent inorganic vitreous microfiber having an average effective diameter of between 0.1 microns and 6 microns. Inorganic vitreous microfibers particularly useful have 18% or more of alkaline oxides and alkaline earth oxides and are non-biopersistent as described previously. Vitreous microfibers can exhibit good fluid handling properties, resiliency, softness, and lack of biopersistence. Inorganic compositions suitable for making microfibers useful in the present invention are described in European Pat. 1048625B, U.S. Pat. No. 6,261,335, and published U.S. Pat. Application No. 2003/0015003. Suitable non-biopersistent inorganic vitreous microfibers are available from Lauscha Fiber International, Summerville, S.C.

The absorbent core lower layer 40 may have at least 5% of superabsorbent polymer.

The absorbent core lower layer 40 can be formed from any suitable materials. Examples of such materials include multiple plies of creped cellulose wadding, fluffed cellulose fibers, wood pulp fibers also known as airfelt, textile fibers, a blend of fibers, a mass or batt of fibers, airlaid webs of fibers, a web of polymeric fibers, and a blend of polymeric fibers.

More typically, the absorbent lower core can be made by air-laying the mixture of fibers and thermoplastic material. In general, air-laying can be carried out by metering an airflow containing the fibers and thermoplastic material, in substantially dry condition, onto a typically horizontally moving wire forming screen. Suitable systems and apparatus for air-laying mixtures 10 of fibers and thermoplastic material are disclosed in, for example, U.S. Pat. No. 4,157,724 (Persson), issued Jun. 12, 1979, and reissued Dec. 25, 1984 as Re. 31,775; U.S. Pat. No. 4,278,113 (Persson), issued Jul. 14, 1981; U.S. Pat. No. 4,264,289 (Day), issued Apr. 28, 1981; U.S. Pat. No. 4,352,649 (Jacobsen et al), issued Oct. 5, 1982; U.S. Pat. No. 4,353,687 (Hosier et al), issued Oct. 12, 1982; U.S. Pat. No. 4,494,278 (Kroyer et al), issued Jan. 22, 1985; U.S. Pat. No. 4,627,806 (Johnson), issued Dec. 9, 1986; U.S. Pat. No. 4,650,409 (Nistri et al), issued Mar. 17, 1987; and U.S. Pat. No. 4,724,980 (Farley), issued Feb. 16, 1988.

Any suitable web forming techniques, including wet laying, which can be suitable for staple fibers, may be used to form a fibrous network having vitreous microfiber staple feedstock. The steps of wet laying includes dispersing vitreous microfiber staple in an aqueous medium. The dispersion is then laid down on a forming screen from a head box or other suitable distribution means, and the aqueous medium drains through the forming screen to form a nascent web, which is then dried and wound to form a rolled web of vitreous microfibers.

A binder can be added to the web to improve mechanical stability of the web. The binder can be thermoplastic binder fibers or powder added to the furnish when the vitreous microfibers are wet laid. The drying step can then be used to melt the binder thereby stabilizing the web. The binder can have a hydrophilic material. The binder can include only a single thermoplastic material. The binder may include a bicomponent fiber having two thermoplastic materials in which one of the materials has a melting point substantially higher than that of the other material so as to preserve fiber integrity when the fiber is exposed to a temperature that causes flow of the thermoplastic material having a lower melting point.

The binder can be a latex binder applied to the wet nascent web as a component of the furnish or after web formation. The latex binder can then be cured in a drying step. The binder can be a polymeric solution (e.g., aqueous polyvinyl alcohol) sprayed on the web which is dried along with the microfibers in the drying step. The binder can be a binding adhesive, such as a hot melt material sprayed on the dried web before the dried web is wound. The hot melt material can be a layer of fiberized hot melt adhesive.

The binder can be a thermosetting wet strength resin applied as a component of the furnish or after formation of the web. For example, a spray application of KYMENE 557H, available from Hercules, Wilmington, Del., can increase the strength of a fibrous network having microfibers. If a small amount of cellulosic fibers such as fibers from the *Eucalyptus* species of tree or crill or similarly classified material is included, additional wet strength materials known in the papermaking arts may be included as a component of the furnish or after web formation. Nonlimiting examples of such materials include and PAREZ 631 NC available from Lanxess, Pittsburgh, Pa., and the aforementioned KYMENE 557H.

Because binders may affect the fluid handling properties of the web, only the minimum amount necessary to obtain sufficient mechanical strength should be used. For a thermoplastic binder, the level can be between 0.1% and 20%. Alternatively, the level for the thermoplastic binder can be between 0.1% and 15%. For post formation binders, the add-on to the dry web can be between 0.1% and 20% or even between 0.1% and 15%.

In addition to webs having binder fibers, other types of fibers may be incorporated into the web to enhance the wet strength and the final strength of the web. Suitable high surface area fibers include micro fibrous cellulose, high surface area cellulosic fibers (e.g., conventional cellulosic pulp fibers, particularly *eucalyptus* fibers, crosslinked cellulosic fibers, including those crosslinked with polyacids such as citric or polyacrylic), and highly refined cellulosic fibers having Canadian Standard Freeness between 1 and 200 can be useful. Fibers having Canadian Standard Freeness of between 40 to 100, referred to herein as "crill," can also be useful.

A portion of the fibers in the web may also include synthetic polymeric or semi-synthetic polymeric fibers. For example, synthetic fibers such as polyester, polypropylene, and polyethylene may be used in relatively small amounts to provide additional strength to the structure. Semi-synthetic fibers, such as rayon, are also suitable. One suitable synthetic fibrous material is CREATE-WL, a short staple (3 mm to 18 mm) polypropylene fiber having a length suitable for wet laying marketed by FiberVisions, Covington, Ga. Other types of synthetic fibers include those termed "bicomponent" fibers wherein a portion of the fiber is of one type and another portion is of another type, often in a coaxial arrangement. An example of a bicomponent fiber is a fiber having a core of polyethylene and a sheath of polypropylene surrounding the core. Other synthetic fibers which may be included are nylon, polyolefins, polyacrylonitrile, polyesters, polyamide, polyaramid, polyacrylates including both polyalkylacrylates and sodium polyacrylates, superabsorbent fibers, and the like. The quantity of such fibers depends on the desired final properties of the web. Alternatively, the fibers can be used in an amount be between 1% and 25%. The fibers can be used at a level between 1% and 15%. The fibers can be used at a level between 1% and 10%.

The web may be airlaid directly after formation of the micro fibers by collecting the fibers on a suitable forming device or by using conventional airlaying techniques used for staple-length fibers. In either case, the web may be formed by a collection of fibers on a foraminous structure. A vacuum system underlying the foraminous structure can aid in gathering the fibers into a web form. Airlaid webs of this type can also use binders and other fibrous materials as described above for wet laid webs.

The web can have a basis weight of between 40 g/m$^2$ and 350 g/m$^2$. Alternatively, the web can have a basis weight between 80 g/m$^2$ and 190 g/m$^2$. Layers of the web may be stacked to achieve higher overall basis weights. The density of the web can be between 0.04 g/cc and 0.25 g/cc. Alternatively, the density of the web can be between 0.07 g/cc and 0.10 g/cc. Micro fibers can include at least 10% of the fibrous assembly.

The absorbent core lower layer 40 can have a substrate layer, a layer of absorbent polymer material, and a layer of adhesive. The substrate layer can for example comprise a fibrous material.

As shown in FIG. 1C, the upper layer 30 of the absorbent core 18 perimeter 66 is asymmetric about the perimeter 66 transverse center line T2. As shown in FIG. 1C, the upper layer 30 of the absorbent core 18 perimeter 66 can include one wholly continuous portion 62.

The absorbent core upper layer 30 perimeter 66 is approximately no greater than 20000 mm$^2$, 16000 mm$^2$, 9000 mm$^2$, 4000 mm$^2$, 1000 mm$^2$, or even less total surface area on any one surface, including, for example approximately 12000 mm$^2$. Alternatively, no greater than 10%, 15%, 20%, 25%, 30%, 35%, 40%, 45%, 50%, 55%, 60%, 65%, 70%, 80%, 85%, 90%, 95%, 100% of the absorbent core upper layer 30 perimeter 66 overlaps with the absorbent core lower layer 40 upper surface 46. Additionally, the absorbent core upper layer 30 may be covered by no greater than 95%, 90%, 85%, 80%, 75%, 70%, 65%, 60%, 55%, 50%, 45%, 40%, 35%, 30%, 25%, 20%, 15%, 10% of the topsheet 14 lower surface 35, such as, for example where the absorbent core upper layer 30 perimeter 66 overlaps with the absorbent core lower layer 40.

The perimeter 66 of the absorbent core upper layer 30 is divided by a transverse axis T2 into upper layer section one 52 and upper layer section two 54. Upper layer section one 52 may have a surface area that is at least 5%, 10%, 15%, 20%, 25%, 30%, 35%, 40%, 45%, 50%, or up to 100% greater than the surface area of section two 54. Upper layer section one 52 may be equal in total surface area to upper layer section two 54. The absorbent core upper layer 30 can be asymmetric about the transverse center line T2 of the absorbent core upper layer perimeter 66. The absorbent core upper layer 30 can be symmetric about the Transverse center line T2 of the absorbent core upper layer perimeter 66. The transverse axis T2 of the perimeter 66 may overlap T1 and/or T. T2 may also be located 5 cm, 4 cm, 3 cm, 2 cm, 1 cm away from T or T1 along the longitudinal center line L2 towards the front or back of the absorbent article.

Figure 4:
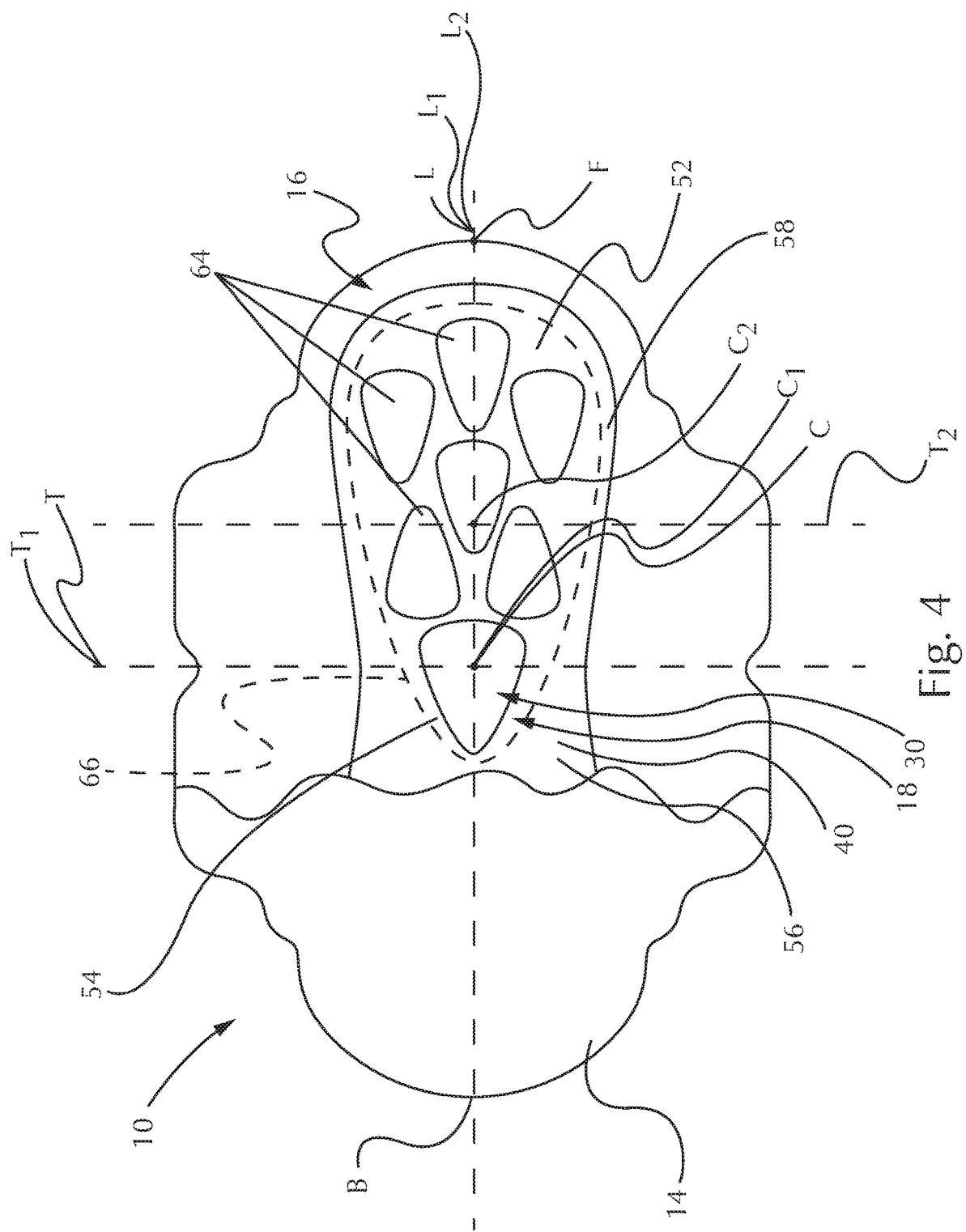
FIG. 4 is a plan view of an absorbent article having an absorbent core containing two separate layers wherein the top layer is discontinuous.

As shown in FIG. 1 and FIG. 4, the upper layer 30 of the absorbent core 18 perimeter 66 may have a continuous portion 62 (as shown in FIG. 1) or of more than one discontinuous portion 64 (as shown in FIG. 4).

The absorbent core upper layer 30 can include open celled foam. One exemplary open-celled foam, High Internal Phase Emulsion (HIPE) foam, is produced from the polymerization of the monomers including the continuous oil phase of a HIPE. HIPE foams may have one or more layers, and may be either homogeneous or heterogeneous polymeric open-celled foams. Homogeneity and heterogeneity relate to distinct layers within the same HIPE foam, which are similar in the case of homogeneous HIPE foams or which differ in the case of heterogeneous HIPE foams. A heterogeneous HIPE foam may contain at least two distinct layers that differ with regard to their chemical composition, physical properties, or both; for example layers may differ with regard to one or more of foam density, polymer composition, specific surface area, or pore size (also referred to as cell size). For example, for a HIPE foam if the difference relates to pore size, the average pore size in each layer may differ by at least 20%, by at least 35%, and by at least 50%. In another example, if the differences in the layers of a HIPE foam relate to density, the densities of the layers may differ by at least 20%, by at least 35%, and by at least 50%. For instance, if one layer of a HIPE foam has a density of 0.020 g/cc, another layer may have a density of at least 0.024 g/cc or less than 0.016 g/cc, in certain embodiments at least 0.027 g/cc or less than 0.013 g/cc, and in still other embodiments at least 0.030 g/cc or less than 0.010 g/cc. If the differences between the layers are related to the chemical composition of the HIPE or HIPE foam, the differences may reflect a relative amount difference in at least one monomer component, for example by at least 20%, in certain embodiments by at least 35%, and in still further embodiments by at least 50%. For instance, if one layer of a HIPE or HIPE foam is composed of 10% styrene in its formulation, another layer of the HIPE or HIPE foam should be composed of at least 12%, and in certain embodiments of at least 15% styrene.

The use of a foam absorbent core upper layer 30 that is smaller in total surface area than the absorbent core lower layer 40 provides a higher absorbency area only where it is needed the most, rather than on the entire surface of the absorbent core lower layer 40. This enables cost savings since foam is only used where it makes the biggest performance impact. The use of a smaller absorbent core upper layer 30 may also act as a signal for improved placement. Traditionally, users use the wings 60 center line to place the absorbent article on the undergarment. The creation of a visible absorbent core upper layer 30 that is smaller in surface area than the absorbent core lower layer 40 allows the consumer to use a different marker versus wings 60 to determine proper placement. For instance, placement in relationship to the body instead of the undergarment may be more intuitive to a user—she can place the absorbent article in the undergarment such that the absorbent core upper layer 30 lines up with her pudendal region. Further, when wings 60 are not present on an absorbent article 10, it is even more important to rely on the absorbent core upper layer 30 to enable correct placement.

A HIPE foam having separate layers formed from differing HIPEs, as explained in more detail below, provides a HIPE foam with a range of desired performance characteristics. For example, a HIPE foam including a first and second foam layer, wherein the first foam layer has a relatively larger pore or cell size, than the second layer, when used in an absorbent article may more quickly absorb incoming fluids than the second layer. By way of example when used in an absorbent articled the first foam layer may be layered over the second foam layer having relatively smaller pore sizes, as compared to the first foam layer, which exert more capillary pressure and drain the acquired fluid from the first foam layer, restoring the first foam layer's ability to acquire more fluid. HIPE foam pore sizes may range from 1 to 200 µm and in certain embodiments may be less than 100 µm. HIPE foams of the present invention having two major parallel surfaces may be from 0.5 to 10 mm thick, and in certain embodiments 2 mm or more. The desired thickness of a HIPE will depend on the materials used to form the HIPE, the speed at which a HIPE is deposited on a belt, and the intended use of the resulting HIPE foam. The HIPE foam may have a thickness of 0.8 mm to 3.5 mm.

The HIPE foams of the present invention are relatively open-celled. This refers to the individual cells or pores of the HIPE foam being in substantially unobstructed communication with adjoining cells. The cells in such substantially open-celled HIPE foam structures have intercellular openings or windows that are large enough to permit ready fluid transfer from one cell to another within the HIPE foam structure. For purpose of the present invention, a HIPE foam is considered "open-celled" if at least 80% of the cells in the HIPE foam that are at least 1 µm in size are in fluid communication with at least one adjoining cell.

In addition to being open-celled, in certain embodiments HIPE foams are sufficiently hydrophilic to permit the HIPE foam to absorb aqueous fluids, for example the internal surfaces of a HIPE foam may be rendered hydrophilic by residual hydrophilizing surfactants or salts left in the HIPE foam following polymerization, by selected post-polymerization HIPE foam treatment procedures (as described hereafter), or combinations of both.

A HIPE foam can be flexible and exhibit an appropriate glass transition temperature (Tg). The Tg represents the midpoint of the transition between the glassy and rubbery states of the polymer. In general, HIPE foams that have a higher Tg than the temperature of use can be very strong but will also be very rigid and potentially prone to fracture. In certain embodiments, regions of the HIPE foams of the current invention which exhibit either a relatively high Tg or excessive brittleness will be discontinuous. Since these discontinuous regions will also generally exhibit high strength, they can be prepared at lower densities without compromising the overall strength of the HIPE foam.

HIPE foams intended for applications requiring flexibility should contain at least one continuous region having a Tg as low as possible, so long as the overall HIPE foam has acceptable strength at in-use temperatures. In certain embodiments, the Tg of this region will be less than 30° C. for foams used at ambient temperature conditions, in certain other embodiments less than 20° C. For HIPE foams used in applications wherein the use temperature is higher or lower than ambient, the Tg of the continuous region may be no more than 10° C. greater than the use temperature, in certain embodiments the same as use temperature, and in further embodiments 10° C. less than use temperature wherein flexibility is desired. Accordingly, monomers are selected as much as possible that provide corresponding polymers having lower Tg's.

The mean cell diameters for open-celled foams can be between 10 and 1,000 microns. The mean densities of open-celled foams can be between 40 kg/m3 and 100 kg/m3. The ability of a structure to "pull" fluid against an opposing force, such as gravity or against affinity for fluid of another substrate with which the structure is in intimate capillary contact, can be characterized by the capillary pressure. The capillary pressure can be characterized as the hydrostatic head at which the vertically wicked fluid loading is 50% of the free absorbent capacity under equilibrium conditions at 31° C. The hydrostatic head is represented by a column of fluid (e.g., synthetic menses). The upper layer 30 can have a capillary pressure of 2 cm to 15 cm.

The open-celled foam disclosed herein can be used in an initially compressed state that expands to full volume as a function of wear time and/or fluid loading. The foam may collapse after an insult of fluid as the lower layer pulls fluid away from the foam.

Figure 2:
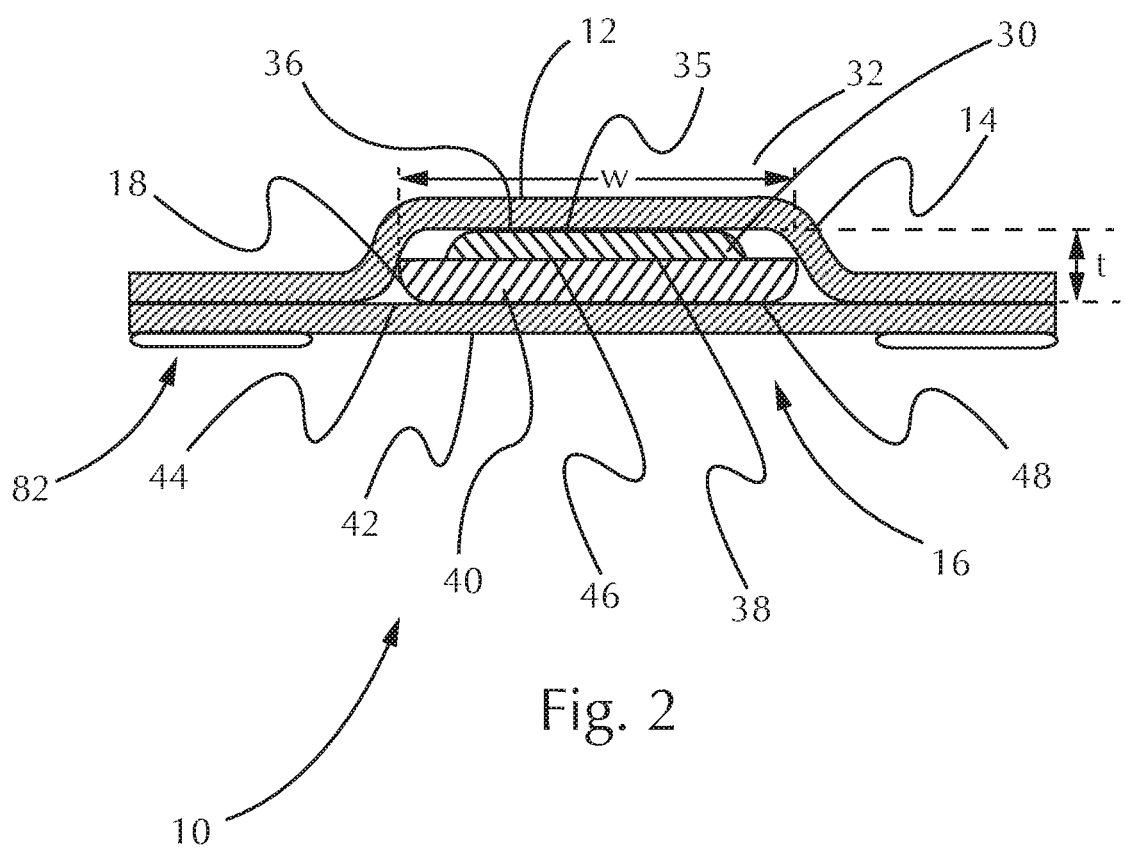
FIG. 2 is a cross section view of an absorbent article of the present invention, taken along the line 1-1 of FIG. 1.

FIG. 2 is an enlarged cross section view of the absorbent article 10 shown in FIG. 1 having a body-contacting surface 12 and a topsheet 14 having an upper surface 32 and lower surface 35 opposite the upper surface 32. The absorbent article 10 has a liquid impervious backsheet 16 joined to the topsheet 14, and an absorbent core 18 disposed between the topsheet 14 and the backsheet 16. The absorbent core 18 has a thickness t and a width w. The backsheet 16 has an upper surface 44 and a lower surface 42 opposite the upper surface 44. The absorbent core 18 has an absorbent core upper layer 30 and an absorbent core lower layer 40. The absorbent core upper layer 30 contains an upper surface 36 and a lower surface 38 opposite the upper surface 36. The upper surface 36 of the absorbent core upper layer 30 may be in direct contact with the lower surface 35 of the topsheet 14. The absorbent core lower layer 40 contains an upper surface 46 and a lower surface 48 opposite the upper surface 46. The lower surface 38 of the absorbent core upper layer 30 is in contact with the absorbent core lower layer 40 upper surface 46. The lower surface 48 of the absorbent core lower layer 40 is in contact with the upper surface 44 of the backsheet. The absorbent article may have an adhesive 82 on the lower surface 42 of the backsheet 16.

Figure 3:
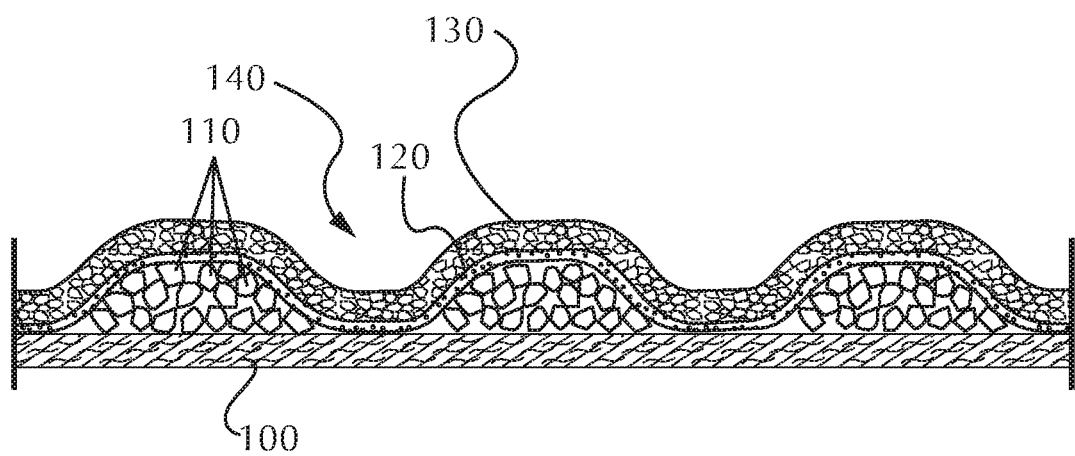
FIG. 3 shows a schematic cross section of an absorbent core lower layer according to one embodiment of the present invention.

FIG. 3 shows a schematic cross section of an absorbent core lower layer 40 according to on embodiment of the present invention. The absorbent core lower layer 40 can have a substrate layer 100, a layer of absorbent polymer material 110, and a layer of adhesive 120. Typically the adhesive can be a hot melt adhesive. In an embodiment of the present invention, the layer of adhesive 120 can be typically for example a layer of fiberized hot melt adhesive 120. The substrate layer 100 can for example comprise a fibrous material.

The substrate layer 100 comprises a first surface and a second surface. Conventionally, in all the sectional views illustrated in the attached drawings the first surface of each layer is meant to correspond to the top surface, in turn, unless stated otherwise, corresponding to the wearer facing surface of the article 20 incorporating the absorbent core, while the second surface corresponds to the bottom surface, hence in turn the garment facing surface. At least portions of the first surface of the substrate layer 100 are in contact with a layer of absorbent polymer material 110. This layer of absorbent polymer material 110 comprises a first surface and a second surface, and can be typically a uniform or non uniform layer, wherein by "uniform" or "non uniform" it is meant that the absorbent polymer material 110 can be distributed over the substrate layer 100 respectively with uniform or non uniform basis weight over the area interested by the distribution. Conversely, the second surface of the layer of absorbent polymer material 110 is in at least partial contact with the first surface of the substrate layer 100. According to an embodiment of the present invention, the layer of absorbent polymer material 110 can also be a discontinuous layer that is a layer typically comprising openings, i.e. areas substantially free of absorbent polymer material, which in certain embodiments can be typically completely surrounded by areas comprising absorbent polymer material. Typically these openings have a diameter or largest span of less than 10 mm, or less than 5 mm, or 3 mm, or 2 mm, or 1.5 mm and of more than 0.5 mm, or 1 mm. At least portions of the second surface of the absorbent polymer material layer 110 are in contact with at least portions of the first surface of the substrate layer material 100. The first surface of the layer of absorbent polymer material 110 defines a certain height of the layer of absorbent polymer material above the first surface of the layer of substrate material 100. When the absorbent polymer material layer 110 is provided as a non uniform layer, typically for example as a discontinuous layer, at least some portions of the first surface of the substrate layer 100 are not covered by absorbent polymer material 110. The absorbent core 28 further comprises a layer of adhesive 120, for example typically a hot melt adhesive. This hot melt adhesive 120 serves to at least partially immobilize the absorbent polymer material 110. According to an embodiment of the present invention, the adhesive 120 can be typically a fiberized hot melt adhesive, i.e., being provided in fibres as a fibrous layer.

In a typical embodiment of the present invention the thermoplastic material 120 can be provided as a fibrous layer which is partially in contact with the absorbent polymer material 110 and partially in contact with the substrate layer 100. In this structure the absorbent polymer material layer 110 is provided as a discontinuous layer, a layer of fiberized thermoplastic material 120 is laid down onto the layer of absorbent polymeric material 110, such that the thermoplastic layer 120 is in direct contact with the first surface of the layer of absorbent polymer material 110, but also in direct contact with the first surface of the substrate layer 100, where the substrate layer is not covered by the absorbent polymeric material 110, i.e. typically in correspondence of the openings of the discontinuous layer of the polymer material 120. By "direct contact" it is meant that there is no further intermediate component layer between the layer of thermoplastic material 120 and the other respective layer in direct contact thereto, such as for example a further fibrous layer. It is however not excluded that a further adhesive material can be comprised between the layer of thermoplastic material 120 and the optional cover layer 130, when present, or the layer of absorbent polymer material 110 or, more typically, the substrate layer 100, such as for example a supplementary adhesive material provided onto the first surface of the substrate layer 100 to further stabilize the overlying absorbent polymer material 110. "Direct contact" can hence be considered to mean in this context a direct adhesive contact between the layer of thermoplastic material 120 and the other respective layer as explained above. This imparts an essentially three-dimensional structure to the fibrous layer of thermoplastic material 120 which in itself is essentially a two-dimensional structure of relatively small thickness (in z-direction), as compared to the extension in x- and y-direction. In other words, the fibrous thermoplastic material layer 120 undulates between the first surface of the absorbent polymer material 110 and the first surface of the substrate layer 100. The areas where the fibrous thermoplastic material 120 is in contact with the substrate layer 100 are the areas of junction 140.

Thereby, the thermoplastic material 120 provides spaces to hold the absorbent polymer material 110 typically towards the substrate layer 100, and thereby immobilizes this material. In a further aspect, the thermoplastic material 120 bonds to the substrate 100 and thus affixes the absorbent polymer material 110 to the substrate 100. Typical thermoplastic materials will also penetrate into both the absorbent polymer material 110 and the substrate layer 100, thus providing for further immobilization and affixation.

As shown in FIG. 4, the absorbent core upper layer 30 perimeter 66 and the absorbent core lower layer 40 may not share the same central transverse axis. Section one 52 of the upper layer 30 may be located over section two 58 of the lower layer 40. The advantage of this orientation is best understood when understanding the interaction between an absorbent article 10 and a woman's body.

Applicants have surprisingly found that using an absorbent core upper layer 30 that contains less surface area than the lower layer 40 and is placed in proximity to the pudendal region further leads to improved reduced wetness on the body. The use of a foam absorbent core upper layer 30 may also allow for the absorbent article 10 lower layer section two 58 to be thinner for improved comfort and fit while lower layer section one 56 is larger as the absorbent article expands towards the back without having absorption. The shape of the perimeter 66 of the absorbent core upper layer 30 may facilitate reduced bunching due to the shape of the continuous portion 62 or the combined effect of the discontinuous portions 64. Applicants have found that shaping the absorbent core upper layer 30 to match a women's pudendal region in terms of area can allow for improved matching to the natural shape of the body while not sacrificing absorbency. Further, the orientation wherein the upper layer 30 section one 52 of the absorbent core is located on top of the lower layer 40 section two 58 can allow for a larger general surface area in the back section of the absorbent article 10 to protect from leaks and undergarment soiling that may not come in direct contact with the pudendal region.

Applicants have also surprisingly found that by manipulating the shape of the absorbent core upper layer 30 and the absorbent core lower layer 40, one can create an absorbent article that has uniform absorptive capacity for each transverse slice moving up the longitudinal axis L of the absorbent article for greater than 80% of the absorbent article 10 while improving the comfort and fit of the absorbent article 10. This can be done using an absorbent core upper layer 30 continuous portion 62 or by using multiple absorbent core upper layer 30 discontinuous portions 64. Traditionally, absorbent articles have to trade off between comfort and absorbency. This is because the increasing absorbency often means increasing width or thickness of the absorbent article 10. Applicants have found that by manipulating the shape of the absorbent core upper layer 30 and the absorbent core lower layer 40, the absorbent article 10 can have improved comfort and fit without having to sacrifice absorbency. The absorbent core upper layer 30 is manipulated to become wider as the absorbent core lower layer 40 is manipulated to become narrower while still being wider than the absorbent core upper layer 30. This improves comfort and fit which may depend on the total width and thickness of the absorbent article while maintaining the preferred level of absorbency. Applicant's absorbent article 10 maintains a minimum level of absorbency throughout 80% or greater of the longitudinal distance of the absorbent article 10 while improving the comfort and fit to the body.

Additionally, Applicants have discovered that the proposed use of an absorbent core 18 having two layers significantly reduces bunching while in use. Bunching occurs when the absorbent article 10 folds upon itself thereby impacting absorption and comfort. Applicants have found that the absorbent core upper layer 30 acts like a memory-like foam that molds to the curves of the body while the absorbent core lower layer 40 fits the design of the undergarment. This reduces the gap between the absorbent article and the body thereby reducing bunching.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article, the absorbent article comprising:
   a topsheet having a body contacting surface and a lower surface opposite the body contacting surface;
   a backsheet joined to the topsheet; and
   an absorbent core disposed between the topsheet and the backsheet,
   wherein the absorbent core comprises an upper layer comprising an upper surface having an upper layer surface area, and a lower surface opposite the upper surface, and a lower layer;
   the upper layer comprising an open celled foam and the lower layer comprising a substrate sublayer, a sublayer of adhesive, and a sublayer of superabsorbent polymer particulate disposed between the substrate sublayer and the sublayer of adhesive;
   wherein the upper layer has a transverse axis,
   the upper layer transverse axis dividing the upper layer surface area into a section one surface area and a section two surface area; and
   wherein the section one surface area is at least 5% greater than the section two surface area.

2. The absorbent article of claim 1 wherein the topsheet comprises apertures.

3. The absorbent article of claim 1 wherein the absorbent article has a first transverse axis and the upper layer has a second transverse axis, and the second transverse axis is 5 cm or less from the first transverse axis.

4. The absorbent article of claim 1 wherein the open celled foam comprises polyurethane.

5. The absorbent article of claim 1 wherein the open celled foam comprises a HIPE foam.

6. The absorbent article of claim 1 wherein the lower layer has a lower layer upper surface having a lower layer surface area, and the upper layer surface area is no greater than 95% of the lower layer surface area.

7. The absorbent article of claim 1 wherein the open celled foam has a thickness between about 0.8 mm to about 3.5 mm.

8. The absorbent article of claim 1 wherein the absorbent core has a total thickness between about 0.8 mm to about 18 mm.

* * * * *